United States Patent [19]
Peterson et al.

[11] Patent Number: 5,629,413
[45] Date of Patent: May 13, 1997

[54] OLIGONUCLEOTIDES WITH ACTIVITY AGAINST HUMAN IMMUNODEFICIENCY VIRUS

[75] Inventors: Todd C. Peterson, Chula Vista; Jorge Velarde, Jr., San Diego, both of Calif.

[73] Assignee: Gen-Probe Incorporated, San Diego, Calif.

[21] Appl. No.: 279,751

[22] Filed: Jul. 19, 1994

Related U.S. Application Data

[63] Continuation-in-part of Ser. No. 94,390, Jul. 19, 1993, abandoned.

[51] Int. Cl.$^6$ .......................... C07H 21/02; C07H 21/04; A61K 31/70
[52] U.S. Cl. .................. 536/23.1; 536/24.1; 536/22.1; 536/23.72; 536/25.3; 435/91.1; 435/91.32; 435/91.33; 435/91.5; 435/91.51; 935/3; 935/5; 935/8; 935/9
[58] Field of Search ........................ 514/44; 536/23.1, 536/23.72, 24.1, 25.3; 435/91.1, 91.32, 91.33, 91.5, 91.51; 935/3, 5, 8, 9

[56] References Cited

U.S. PATENT DOCUMENTS

| | | | |
|---|---|---|---|
| 4,689,320 | 8/1987 | Kaji | 514/44 |
| 4,806,463 | 2/1989 | Goodchild et al. | 435/5 |
| 4,851,330 | 7/1989 | Kohne | 435/6 |
| 5,023,243 | 6/1991 | Tullis | 514/44 |
| 5,110,802 | 5/1992 | Cantin et al. | 514/44 |
| 5,166,195 | 11/1992 | Ecker | 514/44 |
| 5,190,931 | 3/1993 | Inouye | 435/91.32 |
| 5,208,149 | 5/1993 | Inouye | 435/172.3 |
| 5,264,423 | 11/1993 | Cohen et al. | 514/44 |

FOREIGN PATENT DOCUMENTS

| | | |
|---|---|---|
| 0309230 | 3/1989 | European Pat. Off. . |
| 0386563 | 9/1990 | European Pat. Off. . |
| 8902896 | 4/1989 | WIPO . |
| 9115580 | 10/1991 | WIPO . |
| 9207864 | 5/1992 | WIPO . |

OTHER PUBLICATIONS

Rojanasakul 1996 Advances Drug Delivery Reviews 18, 115–131.
Fox 1994 Bio/Technology 12, 128.
Zhu et al. 1993 Science 261, 1179–1181.
Simons 1996 ASM News 62(4), 177–179.
Singleton et al. 1987 in: Dictionary of Microbiology and Molecular Biology (Second Edition) John Wiley and Sons, Chichester, GB, pp. 753–756.
Genesis Report–Rx, vol. 2, No. 4, Jun. 1993, Genesis Group Asssociates (Publ.).
Infectious Disease Weekly, 23 Oct. 1995, C. W. Henderson (Publ.).
Hélèn and Toulmé, "Specific Regulation Of Gene Expression by Antisense, Sence and Antigene Nucleic Acids," *Chemica et Biophysica Acta* 1049:99–125 (1990).
Uhlmann and Peyman, "Antisence Oligonucleotides: A New Therapeutic Principle," *Chemical Reviews* 90:544–584 (1990).
Majumdar et al., "Stepwise Mechanism of HIV Reverse Transcriptase: Primer Function of Phosphorothioate Oligodeoxynucleotide," *Biochemistry* 28:1340–1346 (1989).
Matsukura et al., "Regulation of Viral Expression of Human Immunodeficiency Virus In Vitro by an Antisense Phosphorothioate Oligodeoxynucleotide Against rev (art/trs) in Chronically Infected Cells," *Proc. Natl. Acad. Sci. USA* 86:4244–4248 (1989).
Zuker, "Computer Prediction of RNA Structure," *Methods in Enzymology* 180:262 (1989).
Green et al., "In Vitro Genetic Analysis of the Tetrahymena Self–Splicing Intron," *Nature* 347:406–408 (1990).
Ellington and Szostak, "In Vitro Selection of RNA Molcules That Bind Specific Ligands," *Nature* 346:818–822 (1990).
Bock et al., "Selection of Single–Stranded DNA Molecules That Bind and Inhibit Human Thrombin," *Nature* 355:564–566 (1992).
Burke and Berzal–Herranz, "In Vitro Selection and Evolution of RNA: Applications For Catalytic RNA, Molecular Recognitioin, and Drug Discovery," *FASEB* 7:106–112 (1993).
Nelson, "Detection of Acridinium Esters by Chemiluminescence," *Nonisotopic DNA Probe Techniques*, ed. Larry J. Kricka, (San Diego: Academic Press, Inc., 1992) pp. 275–310.

(List continued on next page.)

*Primary Examiner*—Christopher S. F. Low
*Attorney, Agent, or Firm*—Lyon & Lyon LLP

[57] ABSTRACT

The present invention features compounds and methods for inhibiting propagation of human immunodeficiency virus (HIV). Preferred HIV target sites are identified and oligonucleotides designed to hybridize to a target site are described. The preferred use of the oligonucleotides is as an anti-HIV agent to inhibit HIV propagation in a patient infected with HIV. Other uses of the present invention include detecting the presence of HIV by using the oligonucleotides as detection probes or amplification primers, and measuring the ability of an oligonucleotide to inhibit HIV propagation to evaluate its suitability as an anti-HIV agent for a phenotype of HIV or diagnose the presence of HIV in a patient.

4 Claims, No Drawings

OTHER PUBLICATIONS

Schwartz et al., "Cloning and Functional Analysis of Multiply Spliced mRNA Species of Human Immuodeficiency Virus Type I," *Journal of Virology* 64:2519–2529 (1990).

Goodchild et al., "Inhibition of Human Immunodeficiency Virus Replication by Antisense Oligodeoxynucleotides," *Proc. Natl. Acad. Sci. USA* 85:5507–5511 (1988).

Britten and Davidson, "Hybridization Strategy," in *Nucleic Acid Hybridization—A Practical Approach*, ed. B.D. Hames and S.J. Higgins, (Washington D.C.: IRL Press 1985) pp. 3–15.

Tenover, "Diagnostic Deoxyribonucleic Acid Probes for Infectious Diseases," *Clinical Microbiology Reviews* 1:82–101 (1988).

Liebhaber et al., "Inhibition of mRNA Translation by Antisense Sequences," *Gene Regulation: Biology of Antisense RNA and DNA*, eds. R.P. Erickson and J.G. Izant, (New York: Raven Press, Ltd., 1992) 163–174.

Chatterjee et al., "Dual–Target Inhibition of HIV–1 in Vitro by Means of an Adeno–Associated Virus Antisense Vector," *Science* 258:1485–1488 (1992).

Lomelli et al., "Quantitative Assay Based on the Use of Replicatable Hybridization Probes," *Clin. Chem.* 35(9):1826–1831 (1989).

Ott and Eckstein, "Protection of Oligonucleotide Primers against Degradation by DNA Polymerase I," *Biochemistry* 26:8237–8241 (1987).

Sauvaigo et al., "Standardized Nested Polymerase Chain Reaction–Based Assay for Detection of Human Immunodeficiency Virus Type 1 DNA in Whole Blood Lysates," *J. Chem. Microbiology* 31(5):1066–1074 (1993).

Agrawal et al., "Inhibition of human immunodeficiency virus in early infected and chronically infected cells by antisense oligodeoxynucleotides and their phosphorothioate analogues," *Proc. Natl. Acad. Sci. USA* 86:7790–7794 (1989).

Ratner et al., "Complete nucleotide sequence of the AIDS virus, HTLV–III," *Nature* 313:277–284 (1985).

Morvan et al., "Comparative Evaluation of Seven Oligonucleotide Analogues as Potential Antisense Agents," *J. Med. Chem.* 36:280–287 (1993).

Stein and Cheng, "Antisense Oligonucleotide as Therapeutic Agents—Is the Bullet Really Magical?," *Science* 261:1004–1012 (1993).

Kinchington et al., "A comparison of gag, pol and rev antisense oligodeoxynucleotides as inhibitors of HIV–1," *Antiviral Research* 17:53–62 (1992).

Cantin and Woolf, "Antisense oligonucleotides as antiviral agents: prospects and problems," *Trends in Microbiology* 1:270–276 (1993).

Thierry and Dritschilo, "Intracellular availability of unmodified, phosphorothioated and liposomally encapsulated oligodeoxynucleotides for antisense activity," *Nucleic Acids Research* 20:5691–5698 (1992).

Lisziewicz et al., "Long–term treatment of human immunodeficiency virus–infected cells with antisense oligonucleotide phosphorothioates," *Proc. Natl. Acad. Sci. USA* 90:3860–3864 (1993).

5,629,413

OLIGONUCLEOTIDES WITH ACTIVITY AGAINST HUMAN IMMUNODEFICIENCY VIRUS

RELATED APPLICATION

This application is a continuation-in-part of U.S. application Ser. No. 08/094,390 entitled "Oligonucleotides with Activity Against Human Immunodeficiency Virus," filed Jul. 19, 1993, now abandoned.

FIELD OF INVENTION

This invention relates to oligonucleotides particularly useful in inhibiting replication of the human immunodeficiency virus (HIV).

BACKGROUND OF THE INVENTION

Antisense oligonucleotides can hybridize with viral mRNA and inhibit translation or processing of mRNA, thereby inhibiting viral replication. Hybridization of antisense oligonucleotides to viral mRNA (antisense:mRNA) occurs by hydrogen bonding between complementary nucleotides present on an antisense oligonucleotide and viral mRNA. Adenine (A) is complementary to thymidine (T) and uracil (U), while cytosine (C) is complementary to guanine (G). Along the antisense:mRNA chain classical base pairs AU, TA or UA, GC, or CG are present. Additionally, some mismatched base pairs (e.g., AG, GU) may be present.

The ability to form hydrogen bonds between nucleotides enables antisense oligonucleotides to be targeted to specific viral nucleic acid sequences. Thus, antisense oligonucleotides can be targeted to nucleic acid sequences present only in viral nucleic acid, and vital gene expression can be selectively inhibited.

Oligonucleotides have been claimed as anti-viral agents able to hybridize with viral nucleic acid. For example, Tullis, U.S. Pat. No. 5,023,243 provides a general description of use of antisense oligonucleotides. Kaji, U.S. Pat. No. 4,689,320, provides data showing a decrease in mortality in mice infected with Herpes Simplex Virus when treated with an antisense oligonucleotide having a nucleotide sequence targeted to Herpes Simplex Virus. Goodchild et al., U.S. Pat. No. 4,806,463, provide data to demonstrate the ability of several different specified antisense oligonucleotides to inhibit HTLV-III (HIV) replication, and gene expression in cultured cells infected with HIV. Cantin et al., U.S. Pat. No. 5,110,802, describe the use of a particular methylphosphonate linked oligonucleotide to inhibit HIV replication. Ecker, U.S. Pat. No. 5,166,195, provides data showing the inhibition of a cloned tat gene using certain antisense oligonucleotides (these U.S. patents are hereby incorporated by reference herein). Matsukura et al., *Proc. Natl. Acad.* 86:4244, describe the inhibition of HIV expression in a chronically infected cell without killing the host cell using a phosphorothioate linked oligonucleotide targeted to a rev sequence.

In addition to inhibiting viruses by an antisense mechanism, oligonucleotides can inhibit viruses in a sequence non-specific mechanism. For example, Majumdar et al., *Biochemistry* 28:1340 (1989) describe the use of phosphorothioate oligonucleotides to inhibit HIV reverse transcriptase.

SUMMARY OF THE INVENTION

The present invention describes compounds and methods for inhibiting replication of human immunodeficiency virus (HIV). Preferred HIV target sites are identified and oligonucleotides designed to hybridize to a target site are described. The preferred use of the oligonucleotides is as an anti-HIV agent to inhibit HIV replication in a patient infected with HIV. Other uses of the present invention include detecting the presence of HIV by using the oligonucleotides as detection probes or amplification primers, and measuring the ability of an oligonucleotide to inhibit HIV replication to evaluate its suitability as an anti-HIV agent for a phenotype of HIV or diagnose the presence of HIV in a patient.

The described oligonucleotides are targeted to specific HIV nucleic acid sequences and are believed to inhibit HIV replication by a combination of different mechanisms. One expected mechanism involves hybridization of the oligonucleotide to HIV target nucleic acid thereby inhibiting protein production from the HIV target nucleic acid. Other mechanisms may also play a role in inhibition of HIV replication by the oligonucleotides of this invention. There is no intention to exclude or ignore the possibility that the described oligonucleotides are exerting their effect by mechanisms other than an antisense mechanism. Indeed, phosphorothioate oligonucleotides can inhibit HIV replication by a mechanism not involving oligonucleotide:target hybridization; phosphorothioate oligonucleotides inhibit HIV reverse transcriptase, and may also be able to inhibit gp120 binding and the phosphorylating activity of protein kinase C (PKC).

The described oligonucleotides are targeted to conserved nucleotide sequence regions of the HIV genome coding for proteins necessary for viral replication, namely, mRNA sequences present in the primer binding site (pBS), psi, tat, vpr rev, env, and nef. Several oligonucleotides targeted to a nucleic acid sequence present in tat and vpr ("target site 1," SEQ. ID. NO. 94) or to a nucleotide sequence present in tat, rev, and env, as well as nef mRNA ("target site 2," SEQ. ID. NO. 95) are particularly effective in inhibiting HIV replication. Preferred oligonucleotides are perfectly complementary to a nucleic acid sequence region present in target site 1 or target site 2. Two examples of these preferred oligonucleotides are given by nucleic acid sequence SEQ. ID. NO. 35, which is perfectly complementary to target site 1, and nucleic acid sequence SEQ. ID. NO. 18, which is perfectly complementary to target site 2.

Thus, in a first aspect, the invention features a method for inhibiting HIV replication using a purified oligonucleotide. The method involves the step of contacting cells infected with HIV with a purified oligonucleotide 20 to 100 nucleotides in length. The oligonucleotide is substantially complementary to a nucleic acid sequence region of 20 nucleotides present in an HIV nucleic acid sequence of SEQ ID NO: 94 or SEQ ID NO: 95. The oligonucleotide is expected to inhibit HIV replication by reducing the normal activity of HIV nucleic acid needed for replication, thereby inhibiting HIV replication. Normal activity of HIV nucleic acid needed for replication includes reverse transcription of HIV RNA, synthesis of HIV mRNA, translation of HIV mRNA, processing of HIV mRNA and packaging of genomic HIV RNA.

In vivo hybridization conditions include a physiological temperature of about 37° C. In vivo conditions are low stringency conditions, compared to probe diagnostic hybridization assay conditions, due to their relatively low temperature and hybridization between nucleic acids which are not perfectly complementary can occur. The necessary degree of complementarity for hybridization in vivo or in vitro will be affected by factors such as the segment length of contiguous complementary bases, the type of bases involved in hydrogen bonding (e.g., G:C hydrogen bond formation is stronger that A:T), internal additions or deletions, and structural chemical modification of the oligonucleotide. Preferably two or less, more preferably one or less, most preferably zero, base pairs in a fifteen base stretch of "contiguous" complementary bases are mismatched, are internally deleted, and/or are internally added, compared to a perfectly complementary nucleic acid strand. Complementarity of a particular oligonucleotide to HIV will depend upon the actual HIV strain or isoforms infecting a patient since the base sequence of each HIV type can differ.

By "hybridize" is meant that the antisense oligonucleotide can form a stable duplex (i.e., one that can be detected) with the target HIV nucleic acid and thereby reduce the normal activity of the nucleic acid. Hybridization between the oligonucleotide and the target HIV nucleic acid is preferably specific to targeted viral nucleic acid under in vivo conditions. However, anti-viral oligonucleotides which can form a duplex with both the viral target site and non-target cellular sites under in vivo conditions may still be useful as anti-viral agents in vivo. In vivo effectiveness may be determined by different factors, such as adequate discrimination between inhibition of viral nucleic acid activity and cellular nucleic acid activity, or through an effect on a cellular factor required for HIV expression.

"Substantially complementary to" a nucleic acid sequence means the oligonucleotide is capable of hybridizing to the nucleic acid sequence to form a detectable duplex and preferably has a 0 to 10%, preferably 0 to 5% nucleotide base difference (excluding RNA or DNA equivalent nucleotides), from a nucleic acid perfectly complementary to the nucleic acid sequence. Nucleotide base differences include mismatches, internal additions and/or internal deletions.

The term "purified" refers to an oligonucleotide in a form not found in nature without human intervention. Such oligonucleotides include oligonucleotides isolated, to some extent, and recombined with foreign nucleic acid. Purified oligonucleotides may be produced by techniques known in the art such as chemical synthesis, and in vitro or in vivo expression from recombinant nucleic acid molecules, e.g., retroviral vectors.

Other aspects describe methods of inhibiting HIV replication using a purified oligonucleotide consisting essentially, having, or substantially complementary, to a nucleotide sequence region selected from the group consisting of SEQ. ID. NOs. 18–20 and 22–29, and the RNA equivalents thereto by SEQ. ID. NOs. 65–67 and 69–76 (target site 2); and SEQ. ID. NOs. 35, 38–46, and the RNA equivalents thereto by SEQ. ID. NOs. 82, 85–93 (target site 1).

"Consisting essentially" of a nucleic acid sequence means the oligonucleotide contains a nucleic acid sequence which has 0 to 10%, preferably 0 to 5% nucleotide base difference (excluding RNA or DNA equivalent nucleotides), from the specified nucleotide sequence and has the claimed activity (e.g., anti-HIV activity). Nucleotide base differences include mismatches, internal additions and/or internal deletions. In addition the phrase "consisting essentially" also provides a size limitation of up to 4 additional nucleotides or up to two outside deletions. The additional nucleotides may be complementary, or non-complementary, to HIV nucleic acid.

"RNA and DNA equivalents" refer to RNA and DNA molecules having the same complementary base pair hybridization properties. RNA and DNA equivalents have different sugar groups (i.e., ribose versus deoxyribose), and may differ by the presence of uracil in RNA and thymine in DNA. RNA and DNA equivalents have the same degree of complementarity to a particular sequence.

Preferably, the oligonucleotide is used in the therapeutic treatment of a patient infected with HIV. "Therapeutic" refers to the treatment or prevention of disease caused by HIV infection. A "therapeutically effective amount" is one which inhibits replication of HIV in a patient infected with HIV. Preferably, the therapeutically effective amount relieves, to some extent, one or more symptom associated with HIV infection.

Another aspect describes oligonucleotides targeted to HIV nucleic acid comprising a purified oligonucleotide 20 to 100 nucleotides substantially complementary to a nucleic acid sequence region of 20 nucleotides present in target site 1 or target site 2.

In other aspects, the invention features oligonucleotides having, consisting essentially of, or substantially corresponding to specified nucleic acid sequences targeted (i.e., complementary) to HIV nucleic acid sequences present in target site 1 or target site 2. The specific nucleic acid sequences of oligonucleotides to target site 2 are given by SEQ. ID. NOs. 18–20 and 22–29, and the RNA equivalents thereto by SEQ. ID. NOs. 65–67 and 69–76. The specific nucleic acid sequences of oligonucleotides to target site 1 are given by SEQ. ID. NOs. 35, 38–46, and the RNA equivalents thereto by SEQ. ID. NOs. 82, 85–93.

The oligonucleotides of this invention are generally synthesized in vitro and can be introduced into a cell as a therapeutic composition. The oligonucleotides can also be introduced into a cell by a vector containing the nucleic acid sequences of the target site. Such a vector encodes RNA which can function as an antisense oligonucleotide. See Izant et al., Science 229:345–352 (1985).

The nucleoside subunits of an individual oligonucleotide may be joined by phosphodiester linkages or modified linkages or by non-nucleotide moieties which do not prevent the hybridization properties of the antisense molecule. Modified linkages include those linkages in which a standard phosphodiester linkage is replaced with a different linkage, such as a phosphorothioate, methylphosphonate, phosphodithioate, or phosphoselenate linkage. Modified linkages are generally more resistant to nuclease degradation than phosphodiester linkages.

Oligonucleotide modifications which do not prevent the oligonucleotide from hybridizing to its target nucleic acid are also covered by the present invention. Modified oligonucleotides can have modified sugar groups which do not prevent the oligonucleotide from inhibiting HIV activity or replication. Similarly, oligonucleotides can have modified purine or pyrimidine bases which do not prevent the oligonucleotide from inhibiting HIV.

Oligonucleotides containing phosphorothioate linkages targeted to target sites 1 and 2 were found to inhibit HIV gene expression. Indeed, antisense oligonucleotides targeted to target sites 1 and 2 containing from 13–100 nucleotides covalently joined together are active in this invention.

The invention also features methods for use of the above oligonucleotides, and vectors encoding such oligonucleotides. Other features and advantages of the invention will be apparent from the following description of the preferred embodiments thereof, and from the claims.

DETAILED DESCRIPTION OF THE INVENTION

The present invention concerns oligonucleotides targeted to the HIV genome and mRNA's. The oligonucleotides are designed to hybridize to a particular HIV nucleic acid sequence and are preferably used to inhibit HIV replication. The oligonucleotides have various uses relating to their ability to inhibit HIV replication and/or hybridize to a HIV nucleic acid sequence. Such uses include use as a therapeutic agent and use in diagnostic assays.

An anti-HIV oligonucleotides can be used to inhibit HIV replication alone or in combination with other anti-HIV oligonucleotides or anti-HIV treatments. For example, a first anti-HIV oligonucleotide can be used in combination with a second anti-HIV oligonucleotide. The second anti-HIV oligonucleotide may be either, 1) a subtargeted oligonucleotide, 2) a second separately targeted oligonucleotide, or 3) a non-targeted phosphorothioate oligonucleotide. A subtargeted oligonucleotide is designed to hybridize to a subtarget region of the target region of the first targeted oligonucleotide. Thus, a subtargeted oligonucleotide contains a truncated portion of a first targeted oligonucleotide. An example of a subtargeted/targeted oligonucleotide combination is the phosphorothioate oligonucleotide of sequence SEQ. ID. NO:18 and the phosphorothioate oligonucleotide of sequence SEQ. ID. NO:22, in a 10 to 1 ratio.

The following nucleic acid sequences are provided:

TABLE 1

SEQ. ID. NO. 1: CTTTCAGGTC CCTGTTCGGG CGCCACT,

SEQ. ID. NO. 2: CTTTCAAGTC CCTGTTCGGG CGCCACT,

SEQ. ID. NO. 3: CTTCTAGCCT CCGCTAGTCAAAATTTTT,

SEQ. ID. NO. 4: CTTCTAGCCT CCGCTAGTCAAAAATATT,

SEQ. ID. NO. 5: CTTCTAGCCT CCGCTAGTCAAAATT,

SEQ. ID. NO. 6: CTCCTTCTAG CCTCCGCTAG TCAAAAAT,

SEQ. ID. NO. 7: CTCTCTCCTT CTAGCCTCCG CTAGTCAA,

SEQ. ID. NO. 8: TTAATACTGA CGCTCTCGCA CCCATCT,

SEQ. ID. NO. 9: ACAACAGACG GGCACACACT AACT,

SEQ. ID. NO. 10: GAGAGAGCTC TGGTTTCCCT TT,

SEQ. ID. NO. 11: TCGCCGCCCC TCGCCTCTTG CCGTGC,

SEQ. ID. NO. 12: TCCTGCCATA GGAGATGCCT AAGGCC,

SEQ. ID. NO. 13: TTGATGAGTC TGACTGTTCT GAT,

SEQ. ID. NO. 14: TTGGGAGGTG GGTTGCTTTG,

SEQ. ID. NO. 15: TCTCTCTCTC CACCTTCTTC TTCTAT,

SEQ. ID. NO. 16: TAATCGAATG GATCTGTCTC TGTCTC,

SEQ. ID. NO. 17: GAGCTCTTCG TCGCTGTCTC CGCTTCT,

SEQ. ID. NO. 18: CTTCGGGCCT GTCGGGTCCC CTCGGG,

SEQ. ID. NO. 19: GCCTGTCGGG TCC,

SEQ. ID. NO. 20: GCCTGTCGGG TCCT,

SEQ. ID. NO. 21: CGGGTCCCCT CGGG,

SEQ. ID. NO. 22: GCCTGTCGGG TCCC,

SEQ. ID. NO. 23: CTTCGGGCCT GTCG,

SEQ. ID. NO. 24: CTTCGGGCCT GTCGGGTC,

SEQ. ID. NO. 25: GGGCCTGTCG GGTCCCCT,

SEQ. ID. NO. 26: CTGTCGGGTC CCCTCGGG,

SEQ. ID. NO. 27: TCGGGCCTGT CGGGTCCCCT CG,

SEQ. ID. NO. 28: CTTCGGGCCT GTCGGGTCCC CT,

SEQ. ID. NO. 29: GGGCCTGTCG GGTCCCCTCG GG,

SEQ. ID. NO. 30: TAGGATCTAC TGGCTCCATT TC,

SEQ. ID. NO. 31: ATTGGTACAA GCAGTTTTAG GCT,

SEQ. ID. NO. 32: AGTGGTACAA GCAGTTTTAG GCT,

SEQ. ID. NO. 33: GCTTCTTCCT GCCATAGGAG A,

SEQ. ID. NO. 34: GACTGTTCTG ATGAGCTCTT CGTC,

SEQ. ID. NO. 35: GCCTATTCTG CTATGTCGAC ACCCAA,

SEQ. ID. NO. 36: CGGGCCTGTC GGGTCCCCTC GGGA,

SEQ. ID. NO. 37: CGGGCCTGTC GGGTCCCCTC GGGG,

SEQ. ID. NO. 38: TCTGCTATGT CGAC,

SEQ. ID. NO. 39: ATGTCGACAC CCAA,

SEQ. ID. NO. 40: GCCTATTCTG CTAT,

SEQ. ID. NO. 41: ATTCTGCTAT GTCGACAC,

SEQ. ID. NO. 42: TGCTATGTCG ACACCCAA,

SEQ. ID. NO. 43: GCCTATTCTG CTATGTCG,

SEQ. ID. NO. 44: GCCTATTCTG CTATGTCGAC AC,

SEQ. ID. NO. 45: CTATTCTGCT ATGTCGACAC CC,

SEQ. ID. NO. 46: ATTCTGCTAT GTCGACACCC AA.

Oligonucleotides containing these sequences, consisting of these sequence, containing sequences substantially corresponding to these sequences, consisting essentially of these sequences, are useful in one or more aspects of the present invention.

"Substantially corresponding" refers to an oligonucleotide having a nucleic acid sequence which is identical to, or has no more than a 20% nucleotide base difference (excluding RNA or DNA equivalent nucleotides), from a specified sequence and has the claimed activity (e.g., anti-HIV activity). Nucleotide base differences include mismatches, internal additions and/or internal deletions. Additional nucleotides outside of the specified sequence may be present. The additional nucleotides may be complementary or non-complementary to HIV nucleic acid. Preferably, the substantially corresponding sequence differs by no more than 10%, more preferably no more than 5% from the specified sequence.

I. INHIBITION OF HIV PROPAGATION

Oligonucleotides targeted to HIV target sites 1 and 2, are particularly effective in inhibiting HIV gene expression. Target site 1 is present in exons coding for tat and vpr. Target site 2 is present in exons coding for tat, rev, env, and nef. The presence of the same target site in more than one gene is due to overlapping exons in the HIV genome. As a result of the overlapping exons several genes in the HIV genome contain many of the same nucleic acid sequences in one or more reading frames. Schwartz et al., *Journal of Virology* 64:2519 (1990).

The design of antisense oligonucleotides targeted to HIV is described in detail below. The examples that follow are not limiting in the invention; those skilled in the art will recognize that equivalent oligonucleotides targeted to the regions described below can be readily designed and synthesized, using this application as a guide.

A. Selection Of Target Sites 1 And 2

Antisense oligonucleotides were targeted to conserved HIV nucleic acid sequences having either a weak or a strong secondary structure. The primary sequence of different strains of HIV was obtained from various publications describing the HIV nucleic acid sequence. Antisense oligonucleotides were designed based upon the HIV nucleic acid sequence published for HXB-2 strain of HIV. Conserved primary nucleic acid sequences coding for essential viral proteins were selected by comparing the published HIV sequences for different strains of HIV. The secondary structure was predicted from the primary nucleic acid sequence using methods know in the art (e.g., Zucker, M., In Methods In Enzymology, vol 190, p. 262 (1979)).

Antisense oligonucleotides were targeted to nucleic acid sequences having either a weak or a strong secondary structure, based upon different rationales. A secondary structure arises from the formation of intramolecular hydrogen bonds between complementary nucleotides. The weaker the secondary structure the less likely the formation of intramolecular hydrogen bonds.

B. Design of Antisense Oligonucleotides Targeted To Target Sites 1 and 2

The nucleotide sequences of target sites 1 and 2 are indicated by SEQ. ID. NOs. 94 and 95 respectively. The ability of oligonucleotides having nucleic acid sequences complementary to these sequences to inhibit HIV replication indicate that other antisense oligonucleotides targeted to SEQ. ID. NOs. 94 or 95 will be effective in inhibiting HIV gene expression. SEQ. ID. NOs. 18 and 35, are complementary to SEQ. ID. NOs. 95 and 94, respectively. Both longer versions and truncated versions of SEQ. ID. NOs. 18 and 35 can be used to inhibit HIV replication.

Several factors are important in determining the appropriate versions of SEQ. ID. NOs. 18 and 35 used to inhibit HIV replication. Versions of SEQ. ID. NOs. 18 and 35 must be able to hybridize sufficiently with SEQ. ID. NOs. 95 or 94 under physiological conditions to inhibit nucleic acid activity. Factors affecting hybridization include, base composition, oligonucleotide modifications and oligonucleotide size.

Other factors which are important in oligonucleotide design are the length of the complementary region, the percentage of guanine and cytosine residues, the type of oligonucleotide linkages, and accessibility of the target sequence to hybridization. These factors are known in the art. See, Britten, R. J. and Davidson, E. H., In *Hybridization Strategy In Nucleic Acid Hybridization*, (eds. B. D. Hames and S. J. Higgins) IRL Press, Washington D.C. (1985), hereby incorporated by reference herein. Anti-HIV oligonucleotides are preferably 18 to 50 nucleotides in length, more preferably, 20–35 nucleotides in length. The importance of these factors in a given case can be initially determined in vitro, followed by in vivo studies.

1. Oligonucleotide Modification

Oligonucleotides can be modified to enhance their anti-HIV activity and therapeutic efficacy. Preferred modifications enhance oligonucleotide cellular uptake, oligonucleotide stability, and inhibit HIV propagation. Modified oligonucleotides having increased stability and/or cellular uptake include oligonucleotides having a modified internucleotide linkage, and oligonucleotide modified sugar groups. Examples of modified internucleoside linkages include phosphorothioates, methylphosphonates, and phosphorodithioates. Examples of modified sugar groups include α-anomers and 2'-O-methyloligonucleotides. Cantin and Woolf *Trends in Microbiology* 1:270–276, 1993).

Anti-HIV oligonucleotides preferably contain phosphorothioate linkages. Phosphorothioate linkages increase oligonucleotide stability, facilitate cellular uptake of oligonucleotides, and enable the oligonucleotide to inhibit HIV propagation by a mechanism which appears to be partly sequence independent. Thus, phosphorothioate linked oligonucleotides inhibit HIV by targeting, based on their nucleic acid sequence, a specific HIV target site, and inhibit HIV by a mechanism not dependent on a specific sequence.

Oligonucleotides having phosphorothioate linkages can inhibit viral reverse transcriptase, and may also inhibit gp120 binding to the CD4 receptor and phosphorylating activity of PKC. The viral reverse transcriptase inhibitory effect increases as the size of the phosphorothioate oligonucleotide increases. Oligonucleotides having phosphorothioate linkages are described by Cohen et al., U.S. Pat. No. 5,264,423, and Kinchington et al., *Antiviral Research*, 17:53–62, 1992.

The cell association of phosphorothioate oligonucleotides, in experiments measuring oligonucleotide uptake and stability, was consistently ten times more than for phosphodiester oligonucleotides. Part of this effect appears to be due to cellular uptake of phosphorothioate oligonucleotides being greater than that of phosphodiester oligonucleotides, and part of the effect is attributed to increased phosphorothioate oligonucleotide stability. The difference in uptake mechanisms appears have a greater effect on cell association than the differences in oligonucleotide stability.

Thierry and Dritschilo, *Nucleic Acids Research* 20:5691–5698 (1992), also observed an increase in oligonucleotide uptake and stability due to the presence of phosphorothioate linkages. Thierry found a first oligonucleotide, having 100% phosphorothioate linkages, and a second oligonucleotide, end capped with phosphorothioate groups (i.e., an oligonucleotide having two phosphorothioate modifications at both ends), were both more stable and taken up by a cell to a greater extent then an oligonucleotide having only phosphodiester linkages.

2. Oligonucleotide Size

The optimal oligonucleotide size should take into account several factors including different anti-HIV mechanisms and cellular uptake. Anti-HIV oligonucleotides are preferably 18 to 100 nucleotides in length and contain a preferred nucleic acid sequence or a nucleic acid sequence substantially corresponding to a preferred nucleic acid sequence. Such oligonucleotide are targeted to the identified target site. Additional nucleotides of the preferred nucleic acid sequence may be complementary to HIV nucleic acid or may be non-complementary. More preferably, these oligonucleotides are 18 to 50 nucleotides in length. Most preferably, the oligonucleotide are 20–35 nucleotides in length.

Possible disadvantages of oligonucleotides having a longer length include a decrease in oligonucleotide uptake and a possible increase in cytotoxic effect. The degree of these effects are, at least in part, determined by the size of the oligonucleotide and types of oligonucleotide linkages. Possible cytotoxic effects may be more pronounced, for example, using oligonucleotides containing phosphorothioate linkages.

Oligonucleotides containing longer nucleic acid sequences having complementarity to a target sequence offer several advantages compared to shorter oligonucleotides, including increased target specificity and increased stability of the oligonucleotide:target duplex. The increased stability of the oligonucleotide:target duplex may facilitate the oligonucleotide's HIV inhibitory effect in different ways. For example, if the primary effect is translation arrest, the increased stability of the duplex could increase translation arrest by preventing a ribosome from displacing the oligonucleotide.

Another example of a possible mechanism involves degradation of the RNA strand of an DNA:RNA HIV duplex with an enzyme having RNase H activity. In this instance, the increased stability of the duplex increases the likelihood that the duplex is acted on by the enzyme. To be degraded by RNase H activity, the anti-HIV oligonucleotide in the DNA:RNA HIV duplex preferably contains three or more contiguous phosphodiester or phosphorothioate linkages.

3. Oligonucleotide Complementarity and Melting Temperature

As discussed above, complementary oligonucleotides are designed to hybridize to a target sequence region. While nucleic acids that are not perfectly complementary may hybridize to each other under physiological conditions, the longest stretch of perfectly complementary base sequence generally determines hybrid stability. Oligonucleotides designed to hybridize to a particular sequence region should be designed to have an appropriate melting temperature ($T_m$) (the temperature at which 50% of the oligonucleotide is hybridized to its target nucleic acid). The appropriate $T_m$ can be obtained by varying the probe length and nucleoside composition (percentage of G+C versus A+T). The probe length and nucleoside composition should result in a $T_m$ about 2°–10° C. higher than physiological temperature (37° C.).

The longer the complementary region on an oligonucleotide, the more hydrogen bonding to a target sequence, and in general, the higher the $T_m$. Increasing the percentage of G and C also increases the $T_m$ because G–C base pairs exhibit stronger hydrogen bonding and therefore greater thermal stability than A–T base pairs. $T_m$ can be determined using techniques known in the art such as measuring hybridization by the hybridization protection assay (HPA) according to Arnold et al., entitled "Homogeneous Protection Assay," EPO application number 88308767.8, publication number 309230, and Nelson et al., in *Nonisotopic DNA Probe Techniques*, p. 275 Academic Press, San Diego (Kricka, ed., 1992) (these references are hereby incorporated by reference herein). Oligonucleotides can be labeled with acridinium ester derivatives as described by Arnold, et al., PCT/US88/03361, entitled "Acridinium Ester Labeling and Purification of Nucleotide Probes," hereby incorporated by reference herein.

$T_m$ can be measured using HPA in the following manner. Oligonucleotides are labeled with an acridinium ester. Oligonucleotide:target hybrids are formed in a lithium succinate buffer (0.1M lithium succinate buffer (pH 5.0), 2 mM ethylenediaminetetraacetic acid (EDTA), 2 mM ethylene glycol bis (beta-amino ethyl ether) N, N, N', N' tetraacetic acid (EGTA), 10% (w/v) lithium lauryl sulfate) using an excess amount of HIV RNA target. Aliquots of the solution containing the nucleic acid hybrids are then diluted in the lithium succinate buffer solution. The aliquots are incubated for five minutes at various temperatures starting below that of the anticipated $T_m$ and increasing in 2°–5° C. increments.

This solution is then diluted with a mild alkaline borate buffer (0.15M sodium tetraborate, (pH 7.6), 5% (v/v) TRITON® X-100) non-ionic surfactant and incubated at a lower temperature for ten minutes. Under these conditions the acridinium esters attached to single-stranded oligonucleotides are hydrolyzed, while acridinium esters attached to hybridized oligonucleotides are relatively protected from hydrolysis. Thus, the amount of acridinium esters remaining after hydrolysis treatment is proportional to the number of hybrid molecules present in the sample. The remaining acridinium esters can be measured by monitoring the chemiluminescence produced by addition of hydrogen peroxide and alkali to the solution. Chemiluminescence can be measured in a luminometer (e.g., the Gen-Probe LEADER® I luminometer or LEADER® 50 luminometer). The resulting data is plotted as percent of maximum signal (usually from the lowest temperature) versus temperature. In this assay, the $T_m$ is determined to be the temperature at which 50% of the maximum signal remains. In addition to the method above, $T_m$ may be determined by isotopic methods well known to those skilled in the art (see e.g., Hogan et al., supra).

4. Screening Assay

The oligonucleotide can also be screened by an oligonucleotide screening assay designed to mimic physiological conditions to obtain a measure of the hybridization expected to occur under physiological conditions. Due to the complexity of physiological conditions, the oligonucleotide screening assay provides an approximation rather than an exact prediction of actual hybridization behavior in a cell. An oligonucleotide screening assay can be carried out using a test DNA oligonucleotide, an acridinium ester labeled oligonucleotide having the same nucleotide sequence as the test oligonucleotide, and an enzyme having RNase H activity.

The assay measures the ability of the DNA oligonucleotide to hybridize to an RNA target, thereby forming an DNA:RNA duplex, by measuring the subsequent degradation of the target RNA by RNAse H activity. The acridinium ester labeled oligonucleotide is used to detect remaining target nucleic acids.

An oligonucleotide screening assay can be carried out as follows:

1) Hybridize oligonucleotides to their target nucleic acids in a solution, such as an aqueous physiological buffer. An example of a target nucleic acid is purified HIV mRNA. Hybridization can be carried out using 0.9 pmol of target mRNA, 0.1 pmol acridinium ester-labeled probe, in 100 µL of a physiological buffer, at 37° C. for 2 hours. The reactions are divided to make duplicates at 1× final buffer concentration for optimal RNAse H enzyme activity.

2) *E. coli* RNase H (Life Technologies, Gaithersburg, Md., 0.4 U/reaction) is added to one of the two duplicate reactions. The other duplicate reaction lacks RNase H and serves as the (–) RNase H control. The reactions are incubated at 37° C. for 1 hour, stopped by denaturing at 95° C. for 5 minutes, and placed directly on ice.

3) Aliquots of the reactions are hybridized with the appropriate phosphodiester acridinium ester-probe. Appropriate acridinium ester-labeled probes can hybridize to the same nucleic acid sequence as the test oligonucleotide and contain an acridinium ester in the complementary region. The acridinium ester-probe is hybridized at 60° C. for 1 hour. Control hybridizations are performed using acridinium ester-probes expected to hybridize to a region other than the target nucleic acid sequence.

4) Aliquots are diluted in hybridization buffer (0.1M lithium succinate buffer (pH 5.0), 2 mM EDTA, 2 mM EGTA, 10% (w/v) lithium lauryl sulfate). Fifty microliter replicates are hydrolyzed in 12×75 mm luminometer tubes with 300 µL of 0.15M sodium tetraborate (pH 7.6), 5% (v/v) TRITON® X-100 non-ionic surfactant at 60° C. until non-hybridized labeled probes are fully hydrolyzed (usually 6–8 minutes). Chemiluminescence is brought about using a single injection of 1.5N NaOH, 0.1% $H_2O_2$ and measured in a luminometer.

As would be appreciated by one skilled in the art, variations of this procedure can be performed. For example, the assay can be carried out using different amounts of reagents and incubation times.

C. Therapeutic Activity

The ability of oligonucleotides described herein to inhibit HIV replication is not limited to any particular theory. It is believed that the described oligonucleotides can inhibit viral replication by hybridizing sufficiently in vivo to viral nucleic acid to inhibit viral nucleic acid activity.

1. Discrimination of Target

The described oligonucleotides can function as therapeutic agents by hybridizing sufficiently to viral nucleic acid to inhibit viral nucleic acid activity while not hybridizing sufficiently to essential cellular nucleic acid to inhibit essential cellular nucleic acid activity. Essential cellular nucleic acid activity is nucleic activity needed for cell growth or sustenance. Nucleic acid activity of cellular nucleic acid includes translation and processing of cellular mRNA.

Antisense oligonucleotides which cannot adequately discriminate between viral and essential cellular nucleic acid may be able to act as a therapeutic by being delivered only to HIV infected cells (e.g., using liposomes containing recognition molecules targeted to HIV infected cells).

An estimate of the relative potential activity of different oligonucleotides can be assessed by measuring the hybridization behavior of the oligonucleotide. Exact duplication of in vivo conditions is extremely difficult because the intracellular environment is very complicated and not completely known. Furthermore, there are many nucleic acid binding proteins present in cells which may effect accessibility and activity of viral targets.

In vivo hybridization activity can be modeled in vitro (e.g., using standard physiological saline or 0.12M phosphate buffer pH ~7.0 at 37° C.). Hybridization can be determined using an in vitro quantitative assay, according to Kohne U.S. Pat. No. 4,851,330, or Maniatis et al. *Molecular Cloning*, Cold Spring Harbor Press, N.Y. (1982), both references are hereby incorporated by reference herein. Preferably, antisense oligonucleotides specifically hybridize to target mRNA in vivo. However, absolute specificity is not required. Rather, the antisense oligonucleotide should be able to adequately discriminate between viral and cellular nucleic acid, such that viral propagation can be inhibited without causing significant cell toxicity. Significant cell toxicity occurs when cell growth is inhibited to a greater extent than viral propagation at a particular oligonucleotide concentration. Cell toxicity and compound efficacy can be determined using different techniques. Initial screening can be performed by characterizing the oligonucleotide's ability to hybridize to a target sequence. Subsequent toxicity and/or efficacy tests can be performed using cell cultures and animal models.

The ability to discriminate between cellular and viral nucleic acid activity in vivo can be estimated by measuring specificity of an antisense oligonucleotide in vitro. The measured ratio of efficacy/toxicity for anti-sense mechanisms is expected to increase with increasing specificity. Specificity can be measured under stringent hybridization conditions optimized for this purpose using total cellular nucleic acid. Preferably, acridinium ester (AE) labelled nucleotides are used to determine specificity, and hybridization is detected using the Hybridization Protection Assay (HPA) according to Arnold et al., entitled "Homogeneous Protection Assay," EPO application number 88308767.8, publication number 309230, hereby incorporated by reference herein.

Examples of stringent hybridization conditions for use with AE labelled oligonucleotides include: (1) hybridization at 50° C. for one hour in a solution containing 0.095M lithium succinate pH 5, 0.31M lithium lauryl sulfate, 1.5 mM EDTA, 1.5 mM EGTA; and (2) 0.05M lithium succinate pH 5, 0.6M LiCl, 1% (w/v) lithium lauryl sulfate, 10 mM EDTA, 10 mM EGTA at 50° C. for 15 minutes, followed by the addition of 300 µl of 0.6M sodium borate pH 8.5, 1% TRITON® X-100 non-ionic surfactant at 60° C. for 5–7 minutes.

Hybridization can be judged specific for HIV if the antisense oligonucleotide hybridizes to nucleic acid (total cellular RNA and/or ssDNA) isolated from cells infected with HIV, two times greater than the background signal obtained from the control experiment. The control experiment contains only cellular nucleic acid. Preferably, the signal resulting from hybridization to HIV nucleic acid is at least five times greater than background signal.

2. Administration of Oligonucleotides

The described oligonucleotides are useful for treating patients infected with HIV by inhibiting HIV nucleic acid activity. Anti-viral oligonucleotides can be used to treat HIV patients using different formulations and routes of administration. Suitable routes of administration include intramuscular, aerosol, oral (tablet or pill form), topical, systemic, ocular, intraperitoneal and intrathecal.

Antisense oligonucleotides may be introduced as naked oligonucleotide, through expression vectors (encoding such antisense molecules), or as physiologically acceptable formulations. Suitable formulations include the use of a liposome, a controlled release vehicle, by use of iontophoresis, ion paired molecules, covalently attached adducts, and other pharmacologically suitable methods of delivery.

Different types of delivery strategies are useful in the present invention, including: oligonucleotide modifications, particle carrier drug delivery vehicles, and retroviral expression vectors. Antisense oligonucleotides joined by phosphodiester linkages are slowly taken up by cells. To enhance cellular uptake, the antisense oligonucleotide may be modified at the phosphodiester linkage to reduce its charge. For example, the individual nucleotides may be joined by methylphosphonate linkages.

Modification of antisense to reduce charge is just one approach to enhance the cellular uptake of these larger molecules. Modifications can also be designed to reduce susceptibility to nuclease degradation (e.g., use of phosphorothioate linkages).

Drug delivery vehicles can be chosen for both systemic and topical administration. These vehicles can be designed to serve as a slow release reservoir or to deliver their contents directly to the target cell. An advantage of using direct delivery drug vehicles is that multiple molecules are delivered per uptake. Such vehicles have been shown to increase the circulation half-life of drugs which would otherwise be rapidly cleared from the blood stream. Some examples of such specialized drug delivery vehicles which fall into this category are liposomes, hydrogels, cyclodextrins, biodegradable nanocapsules, and bioadhesive microspheres.

The use of liposomes as a drug delivery offers several advantages. Liposomes increase intracellular stability, increase uptake efficiency and improve biological activity. Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver nucleic acids to cells and that the nucleic acid remains biologically active. For example, a liposome delivery vehicle originally designed as a research tool, Lipofectin, can deliver intact nucleic acid molecules to cells.

Specific advantages of using liposomes include the following: they are non-toxic and biodegradable in composition; they display long circulation half-lives; and recognition molecules can be readily attached to their surface for targeting to tissues. Finally, cost effective manufacture of a liposome-based pharmaceutical, either in a liquid suspension or lyophilized product, has demonstrated the viability of this technology as an acceptable drug delivery system.

Antisense oligonucleotides may be systemically administered. Systemic absorption refers to the accumulation of drugs in the blood stream followed by distribution throughout the entire body. Administration routes which lead to systemic absorption include: intravenous, subcutaneous, intraperitoneal, intranasal, intrathecal and ophthalmic. Each of these administration routes expose the antisense oligonucleotide to accessible diseased cells. Subcutaneous administration drains into a localized lymph node which proceeds through the lymphatic network into the circulation. The rate of entry into the circulation has been shown to be a function of molecular weight or size. The use of a liposome or other drug carrier can localize the antisense oligonucleotide at the lymph node. The antisense oligonucleotide can be modified to diffuse into the cell, or the liposome can directly participate in the delivery of either the unmodified or modified antisense oligonucleotide to the cell.

A liposome formulation which can associate antisense oligonucleotides with the surface of lymphocytes and macrophages is also useful. This will provide enhanced delivery to HIV-infected cells by taking advantage of the specificity of macrophage and lymphocyte immune recognition of infected cells.

Intraperitoneal administration also leads to entry into the circulation with the molecular weight or size of the antisense oligonucleotide-delivery vehicle complex controlling the rate of entry.

The chosen method of delivery will result in intracellular accumulation of the composition in the afflicted cells. Nuclear delivery may be used but is less preferable. The accumulation of oligonucleotide in a particular compartment will be largely effected by oligonucleotide charge and chemistry. Most preferred delivery methods include liposomes (10–400 nm), hydrogels, controlled-release polymers, microinjection or electroporation (for ex vivo treatments) and other pharmaceutically applicable vehicles.

The exact dosage and number of doses will depend upon the efficacy data from clinical trials. Several factors such as the delivery vehicle, disease indication, the route of administration, and the linkage joining the oligonucleotide will affect the dosage. The expected dosage is between 0.001–200 mg/kg of body weight/day. The duration of treatment will extend through the course of the disease symptoms. Multiple daily doses are anticipated for topical applications, ocular applications and vaginal applications.

Establishment of therapeutic levels of antisense oligonucleotides within the cell is dependent upon the rate of uptake and degradation. Decreasing the degree of degradation prolongs the intracellular half-life of the antisense oligonucleotide. Thus, chemically modified antisense oligonucleotides, e.g., with modification of the phosphate backbone, are preferred.

3. HIV Protection Assay

Anti-HIV oligonucleotides can also be used in assays measuring the ability of the oligonucleotide to inhibit HIV cytopathic effects. These assays have various uses including use to identify or confirm the presence of HIV as a disease causing agent in a person, use to determine which oligonucleotide to administer to a patient, and use to evaluate the initial effectiveness of an oligonucleotide.

An HIV protection assay can be carried using anti-HIV oligonucleotides and standard techniques for measuring cell growth. Techniques which can be used as a measure of cell growth include the use of dyes such as XTT (2,3-bis [2-methoxy-4-nitro-5-sulphophenyl]-2H-tetrazolium-5-carboxanilide) to measure the cells metabolic state, the use of radioactive or modified nucleotide precursors such as BUdR (bromodeoxyuradine) to measure nucleic acid replication, and the use of oligonucleotides complementary to host nucleic acids to measure production of host nucleic acids.

Assays involving oligonucleotides complementary to cellular nucleic acids can be carried out using an oligonucleotide containing a detectable label such as fluorescent, chemiluminescent, enzyme or radioactive label. Oligonucleotides can be designed to hybridize to host nucleic acid sequence regions such as those present in DNA, mRNA or rRNA. Examples of such nucleotide sequence regions are known in the art and can be obtained by standard techniques. The preferred source of host target nucleic acids to test for growth of host cells is rRNA. A nucleic acid having a nucleotide sequence characteristic of rRNA is generally present in a cell in much greater abundance than a nucleic acid sequence present in mRNA.

HIV infects cells containing a CD4 antigen (CD4$^+$). The major target cell population is T-helper lymphocytes and cells of the monocyte/macrophage lineage. The HIV-protection assay can be performed on such cells from persons suspected of being infected with HIV. The assay can be performed in vitro directly on such cells taken from the patient, or can be performed using lysates obtained from CD4$^+$ cells. The lysate can be used to infect cells more susceptible to the HIV cytopathic effect than the isolated cells.

An HIV protection assay can be carried out as follows:
1) Isolate CD4$^+$ cells from a person. Preferred cells are T-lymphocytes.
2) Incubate cells under conditions compatible with cell growth in the presence (treated cells) and absence (control cells) of an anti-HIV oligonucleotide. Examples of conditions compatible with cell growth are described by S. Gartner and M. Popovic, 1990, Virus Isolation and Production, pp. 53–70 in *Techniques in HIV Research*, ed. by A. Alaldocini and B. D. Walker. Stockton Press. N.Y.
3) Measure the growth of the treated and control cells at one or more time points after exposure of cells to the oligonucleotides.

Normal growth of control cells indicates the absence of a viral infection such as an HIV infection. Normal growth can be determined by comparing the growth of the control cells to the same type of cells which are known to be healthy.

Less than normal growth of control cells indicates the presence of some cellular disorder, such as HIV. The ability of an anti-HIV oligonucleotide to protect against HIV cytotoxicity in treated cells indicates the disorder is due to HIV and that the tested anti-HIV oligonucleotide can be used to treat the patient. The inability of an anti-HIV oligonucleotide to inhibit HIV in this assay cell toxicity may at times fail to correctly indicate the presence of HIV due to the variability in nucleic acid sequences of different strains of HIV. Thus, an HIV protection assay should be used along with other assays known in the art to detect the presence of HIV. Because of the severity of AIDS, and the possible adverse effect an incorrect diagnosis of HIV could have, the HIV protection assay is preferably used to confirm the presence of HIV and make an initial determination regarding the suitability of a specific oligonucleotide to treat a patient infected with HIV. Patients determined to be infected with HIV by other assays, but not by the HIV protection assay, should be retested using the HIV protection assay in conjunction with a different oligonucleotide.

II. DETECTION OF HIV BY OLIGONUCLEOTIDE HYBRIDIZATION

Oligonucleotides targeted to HIV nucleic acids can also be used as detection probes to measure the presence of a HIV target sequence and as amplification primers to selectively amplify HIV nucleic acid. Hybridization to either the target nucleic acid or a nucleotide sequence region complementary to the target sequence is useful for detecting the presence of HIV. Production of nucleic acids having nucleotide sequences complementary to a target nucleic acid can be obtained using the target nucleic acid as a template in amplification reactions such as polymerase chain reaction (PCR) or transcription mediated amplification methods (e.g., Kacian and Fultz, entitled "Nucleic Acid Amplification Methods," EPO application number 90307503.4).

Useful guidelines for designing probes for HIV detection and amplification primers are described herein and include considerations discussed above, relating to the hybridization of an oligonucleotide to a nucleic acid bearing its complementary sequence. These considerations should be considered in light of the different hybridization conditions under which the oligonucleotides operate. Anti-HIV oligonucleotides are usually used under physiological conditions. In contrast, amplification primers and detection probes can be used under a wider range of conditions, and are preferably used under stringent hybridization assay conditions.

A target nucleotide sequence region present on a nucleic acid molecule is amplified using a primer 5' of the target nucleotide sequence region and a primer 3' of the target nucleotide sequence region. The optimal sites for primer binding are conserved nucleotide sequence regions greater than about 15 bases in length, within about 350 bases, and preferably within 150 bases, of contiguous sequence. Amplification primers are designed to hybridize to these regions. A promoter can be attached to the primer for transcription mediated amplification.

The degree of amplification observed with a set of primers or promotor/primers depend on several factors, including the ability of the oligonucleotides to hybridize to their complementary sequence regions and to be extended enzymatically. Because the extent and specificity of hybridization reactions are affected by several factors, manipulation of those factors determines the exact sensitivity and specificity of a particular oligonucleotide, whether or not it is perfectly complementary to its target. The importance and effect of various assay conditions are known to those skilled in the art and are described in references such as Hogan et al., EPO Patent Application No. PCT/US87/03009, entitled "Nucleic Acid Probes for Detection and/or Quantitation of Non-Viral Organisms."

Oligonucleotide detection and amplification probes of a variety of lengths and base compositions may be used, however, preferred probes are between 18 to 100 nucleotides in length, more preferably 18 to 50 nucleotides in length and are sufficiently complementary to the target nucleic acid to hybridize under stringent hybridization conditions (e.g., conditions where probe oligonucleotide hybridizes to an HIV target sequence region and not to human nucleic acids or nucleic acid from other organisms). Optimal primers have target-binding regions of 18–38 bases, with a predicted Tm (melting temperature) for the target:primer duplex of about 65° C.

Oligonucleotide detection probes and amplification primers should be designed to minimize the stability of oligonucleotide:nontarget nucleic acid hybrids. The probes should be able to distinguish between target and non-target nucleotide sequence regions under stringent hybridization conditions. In designing probes, the differences in Tm values between oligonucleotide:target and oligonucleotide:nontarget duplexes should be as large as possible (e.g., at least 2° C. and preferably 5° C.).

The secondary structure of the probe and the target region also affects hybridization. Regions of the nucleic acid forming strong internal structures inhibitory to hybridization are less preferred target sites. Examples of such structures include hairpin stem-loop structures. Likewise, probes with extensive self-complementarity should be avoided. Intramolecular and intermolecular hybrids can form within a probe if there is sufficient self complementarity. Such structures can be avoided through careful probe design. Commercial computer programs are available to search for these types of interactions. Available computer programs include MacDNASIS™ 2.0 (Hitachi Software Engineering American Ltd.) and OLIGO® ver. 4.1 (National Bioscience).

An integrated genomic target nucleotide sequence region naturally occurs in a double stranded form, as does the product of the polymerase chain reaction (PCR). These double-stranded target nucleic acids inhibit probe:target hybridization. Double stranded target can be accessible before the hybridization step using standard techniques such as heat denaturation.

The rate of hybridization can be determined by measuring the $C_ot_{1/2}$. The rate at which an oligonucleotide hybridizes to its target partly depends on the thermal stability of the secondary structure of the target nucleic acid in the region complementary to the probe. The standard measurement of hybridization rate is the $C_ot_{1/2}$ which is measured as moles of nucleotide per liter times the time in seconds it takes for 50% of the nucleic acids to hybridize. Thus, the $C_ot_{1/2}$ is the concentration of free probe times the time at which 50% of maximal hybridization occurs at that concentration. This value is determined by hybridizing various amounts of probe to a constant amount of target for a fixed time. The $C_ot_{1/2}$ is found graphically by standard procedure.

The degree of non-specific primer extension (primer-dimer formation or non-target copying) can affect amplification efficiency. Therefore, primers preferably have low self- or cross-complementarity, particularly at the 3' end. Long homopolymer tracts and high GC content should be avoided to reduce spurious primer extension. Commercial computer programs are available to aid in this aspect of the design. Available computer programs include MacDNA-SIS™ 2.0 (Hitachi Software Engineering American Ltd.) and OLIGO® ver. 4.1 (National Bioscience).

Once synthesized, detection probes may be labeled using well known methods (J. Sambrook, E. F. Fritsch and T. Maniatis, *Molecular Cloning*, Chapter 11 (2d ed. 1989). Useful labels include fluorescent, chemiluminescent, enzyme and radioactive groups.

III. SYNTHESIS OF OLIGONUCLEOTIDES

Oligonucleotides containing phosphodiester linkages as well as modified linkages can be synthesized by procedures known in the art. For example, Caruthers, et al., In *Methods In Enzymology* vol. 154 p. 287 (1987), describe a procedure for synthesizing oligonucleotides containing phosphodiester linkages by standard phosphoramidite solid-phase chemistry; Bhatt, U.S. Pat. No. 5,252,723 describes a procedure for synthesizing oligonucleotides containing phosphorothioate linkages; and Klem et al. entitled "Improved Process for the Synthesis of Oligomers" PCT WO92/07864, describe the synthesis of oligonucleotides having different internucleotide linkages including methylphosphonate linkages.

IV. EXAMPLES

Examples are provided below to illustrate different aspects and embodiments of the present invention. These examples are not intended in any way to limit the disclosed invention.

Example 1: Viral Inhibition By Antisense Oligonucleotides

This example demonstrates the ability of different antisense oligonucleotides to inhibit HIV replication. The effect of several phosphorothioate antisense oligonucleotides on HIV replication was determined by measuring p24 (an HIV-specific polypeptide) produced by 8e5 cells. The 8e5 cell line is a human T-cell line that generates replication defective HIV (Folks et al. U.S. Pat. No. 4,752,565). The defective HIV contains a single integrated provirus that expresses all HIV proteins at levels typically observed in chronically infected cell lines except those encoded by pol. This defect is due to a single base insertion that causes a frame shift mutation in pol.

Oligonucleotides having phosphorothioate linkages were synthesized according to Bhatt supra. Synthesized oligonucleotides were purified using HPLC, extracted with ethyl acetate, ethanol precipitated, washed with 80% ethanol and suspended in sterile water to generate high concentration stock solutions that facilitated small volume addition (2–20 µl).

8e5 cells were cultured in 24 well plates under conditions that resulted in maximal p24 production over the experimental time course. Phosphorothioate antisense oligonucleotides were added directly to 8e5 cultures. Sterile water and non-specific phosphorothioate oligonucleotides were utilized as controls. The cultures were harvested after 4 days, and the viable cell count and production of p24 antigen were determined. Cell lysates were prepared by spinning down cells from 2 ml wells at 1000 rpm for 10 minutes at 4° C. using a Beckman J-10, and removing the supernatant. The cells were then washed with 5 ml of Hanks balanced salt solution (Gibco) or sterile saline solution (0.9% NaCl), and spun down at 1000 rpm for 10 minutes at 4° C. using a Beckman J-10. The cells were resuspended in 300 µl of TSM (10 mM Tris-HCl pH 7.5, 150 mM NaCl, 2 mM $MgCl_2$) with 0.5% NP-40, and incubated on ice for 5 minutes. The nuclei and cellular debris were then spun down at 2000 rpm using a Beckman J-10. The amount of p24 antigen was determined in cell lysates using a p24 capture ELISA (American Biotechnologies, Inc.).

The ELISA assay for p24 was selected as a measure of HIV replication because expression of tat and rev are required for efficient p24 production. The percentage of HIV p24 production was calculated as p24/cell production by antisense treated cells divided by p24/cell production by control treated cells. Control treated cells were treated with a random control phosphorothioate oligonucleotide (SEQ. ID. NO. 47: AGGCTTCATC ACGTGGACAT TGACG).

As shown in Table 2, several different antisense oligonucleotides inhibited HIV production. The most effective antisense oligonucleotides tested have the nucleic acid sequences SEQ. ID. NOs. 18 or 35. The inhibition with these oligonucleotides ranged from 70–100% (0 to 30% p24 production). The data in Table 2 show the results of a particular experiment. Some of the other antisense oligonucleotides tested caused an increase in the percentage of p24 relative to the control. This phenomena is not well understood.

TABLE 2

INHIBITION OF HIV EXPERIMENT USING PHOSPHOROTHIOATE ANTI-HIV OLIGONUCLEOTIDES

| Oligonucleotide SEQ. ID. NO. | Concentration µM | % p24 production |
|---|---|---|
| 14 | 2 | 103 |
| 14 | 10 | 66 |
| 17 | 2 | 99 |
| 17 | 10 | 56 |
| 18 | 2 | 55 |
| 18 | 10 | 0 |
| 31 | 2 | 100 |
| 31 | 10 | 15 |
| 33 | 2 | 109 |
| 33 | 10 | 74 |
| 35 | 2 | 56 |
| 35 | 10 | 0 |
| 36 | 2 | 71 |
| 36 | 10 | 89 |

Several different truncated versions of oligonucleotides having the nucleic acid sequence of SEQ. ID. NOs. 18 or 35 were tested for their ability to inhibit HIV replication. These results are shown in Table 3.

TABLE 3

INHIBITION OF HIV EXPERIMENT USING SMALL LENGTH PHOSPHOROTHIOATE ANTI-HIV OLIGONUCLEOTIDES

| Oligonucleotide SEQ. ID. NO. | Concentration µM | % p24 production |
|---|---|---|
| 20 | 10 | 55 |
| 20 | 20 | 42 |
| 22 | 10 | 3 |
| 22 | 20 | 31 |
| 26 | 20 | 44 |
| 29 | 10 | 79 |
| 29 | 20 | 58 |

TABLE 3-continued

INHIBITION OF HIV EXPERIMENT USING
SMALL LENGTH
PHOSPHOROTHIOATE ANTI-HIV OLIGONUCLEOTIDES

| Oligonucleotide SEQ. ID. NO. | Concentration μM | % p24 production |
|---|---|---|
| 46 | 10 | 87 |
| 46 | 20 | 81 |

As seen in Table 3, several truncated version of SEQ. ID. NO. 18 (SEQ. ID. NOs. 20, 22, 26, and 29), were particularly effective in inhibiting p24 production. In addition, truncated version of SEQ. ID. NO. 35 (SEQ. ID. NO. 46), was effective in inhibiting p24 production. Other appropriate truncated versions can be selected based upon the disclosure provided herein.

Example 2: Viral Inhibition Using Different HIV Strains

The ability of an antisense oligonucleotide to inhibit HIV replication is shown below using different cells infected with different strains of HIV. The nucleic acid sequence of the oligonucleotide used in this experiment is given by SEQ. ID. NO. 18. The nucleoside groups of the oligonucleotide were joined by phosphorothioate groups and contained deoxyribose moieties.

HeLa-CD4 cells were tested using a plaque assay as described below. Specific cells (as described in Table 4) were detached using trypsin-EDTA for 8–10 minutes at 37° C. The cells were then centrifuged at 100 rpm for 10 minutes. Cells were resuspended in 5–10 ml of maintenance medium (Dulbecco's Modified Eagle Medium ("DMEM") containing 10% fetal calf serum, 500 unites/mg penicillin, 500 units/mg streptomycin, and 2 mM glutamine). Cells were maintained by splitting the culture once weekly into two 75 cm$^2$ T-flasks at a concentration of 3×10$^4$ cells/ml in a total volume of 200 ml maintenance medium.

On day 0, the cells were plated into the wells of a 24 well tissue culture plate (Falcon #3047) at a concentration of 2.4×10$^4$ cells per well. The cells were incubated overnight at 37° C. The next day the medium was aspirated, and 200 μl of HIV virus at a multiplicity of infection ("MOI") of 0.03 was added to each well. The plates were then incubated for 2 hours at 37° C. After the 2 hour incubation, the cells were treated with 800 μl of drug at a concentration (in DMEM) of 1.25× of the final concentration.

The treated cells were incubated for 3 days at 37° C. On day 4 the plate was fixed with 1 ml/well of 100% methanol for 15 minutes. The wells were then aspirated and 0.5 ml of 0.3% crystal violet stain was added to the wells. After 5 minutes the wells were washed with water and dried. Plaques were counted using a microscope. The number of plaques was plotted versus the concentration of the antisense oligonucleotide. From the plot IC$_{50}$ was determined and the results are presented in Table 4.

TABLE 4

INHIBITION OF DIFFERENT HIV STRAINS USING THE
OLIGONUCLEOTIDE OF SEQ. ID. NO. 18

| Cell Type | HIV Virus Strain | Drug | Assay Criterion | IC$_{50}$ |
|---|---|---|---|---|
| HeLa-CD4 | HIV-1 (LAI) | phosphorothioate SEQ. ID. NO. 18 | plaques formed | 200 nM |
| HeLa-CD4 | HIV-1 (LAI) | AZT | plaques formed | 7–20 nM |
| HeLa-CD4 | Patient Isolates (AO18) AZT Sensitive AZT Resistant | phosphorothioate SEQ. ID. NO. 18 | plaques formed | 80 nM 55 nM |
| HeLa-CD4 | Patient Isolates (PO22) AZT Sensitive AZT Resistant | phosphorothioate SEQ. ID. NO. 18 | plaques formed | 45 nM 18 nM |
| HeLa-CD4 | HIV-2 (ROD) | phosphorothioate SEQ. ID. NO. 18 | plaques formed | 18 nM |
| PBMC | HIV-1 (LAI) | AZT | p24 | 3 nM |
| PBMC | HIV-1 (LAI) | phosphorothioate SEQ. ID. NO. 18 | p24 | 120 nM |

Example 3: Pharmacological Studies

This example describes pharmacological studies to evaluate the cytotoxicity of anti-HIV oligonucleotides. The nucleic acid sequence of the oligonucleotides used in this example are SEQ. ID. NOs:18 and 22. These oligonucleotides contained phosphorothioate linkages.

The cytotoxicity of the test oligonucleotides was determined in a system using primary human blood cells using techniques known to those of skill in the art to measure cytotoxicity of anti-neoplastic agents. Human bone marrow cells were harvested and washed in an isotonic solution, then incubated in tissue culture medium containing 0.3% (w/v) agar, 20% (v/v) fetal calf serum, and 10 ng/ml granulocyte-colony stimulating factor with varying amounts of the two test oligonucleotides. The number of colonies formed were measured after eight days in culture. The IC$_{50}$ for colony formation in this experiment was 2–3 μM for SEQ. ID. NO:18 and 20–30 μM for SEQ. ID. NO:22.

In vivo experiments were also performed using rodent models. These experiments focused on the potential for gross morphological changes in blood tissue upon administration of a phosphorothioate linked oligonucleotide having the nucleic acid sequence of SEQ. ID. NO:18 (in a solution of PBS). Three mice were given the oligonucleotide at a dose of 100 mg/kg body weight. Four control mice were given PBS alone. Blood samples were taken from each animal at t=0, and at 24 hours each animal was sacrificed and the organs removed. The experimental findings with regard to blood parameters are shown in Table 5, and the results obtained upon visual inspection of the organs are shown in Table 6.

TABLE 5

EFFECT OF ANTI-HIV OLIGONUCLEOTIDE ON BLOOD PARAMETERS

| PBS (n=4) | 0 hr | 24 hr |
|---|---|---|
| RBC (×10$^4$/μl) | 1035.0 ± 22.4 | 1019.9 ± 49.7 |
| WBC (×10$^2$/μl) | 92.5 ± 19.0 | 82.0 ± 12.9 |
| PLT (×10$^4$/μl) | 117.4 ± 7.6 | 118.3 ± 7.1 |
| HGB (g/dl) | 16.1 ± 0.3 | 16.0 ± 0.6 |

| SEQ. ID. NO. 18 (n=3) | 0 hr | 24 hr |
|---|---|---|
| RBC (×10$^4$/μl) | 1032.3 ± 8.1 | 990.3 ± 34.3 |
| WBC (×10$^2$/μl) | 94.7 ± 18.2 | 79.3 ± 15.3 |
| PLT (×10$^4$/μl) | 111.8 ± 2.7 | 99.4 ± 0.9 |
| HGB (g/dl) | 16.0 ± 0.2 | 15.3 ± 0.5 |

"RBC" refers to red blood cells. "WBC" refers to white blood cells. "PLT" refers to platelets. "HGB" refers to hemoglobin.

TABLE 6

MORPHOLOGICAL EFFECT OF PHOSPHOROTHIOATE LINKED OLIGONUCLEOTIDE OF SEQ. ID. NO. 18

| Body Weight | Unchanged |
|---|---|
| Morphological findings | |
| Bone Marrow | Normal |
| Liver | Normal |
| Kidney | Normal |
| Heart | Normal |
| Thymus | Normal |
| Spleen | Slight Splenomegaly |

Other embodiments are within the following claims.

We claim:

---

SEQUENCE LISTING ( 1 ) GENERAL INFORMATION:

( i i i ) NUMBER OF SEQUENCES: 95

( 2 ) INFORMATION FOR SEQ ID NO: 1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 1:

```
CTTTCAGGTC CCTGTTCGGG CGCCACT                                    27
```

( 2 ) INFORMATION FOR SEQ ID NO: 2:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 2:

```
CTTTCAAGTC CCTGTTCGGG CGCCACT                                    27
```

( 2 ) INFORMATION FOR SEQ ID NO: 3:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 3:

```
CTTCTAGCCT CCGCTAGTCA AAATTTTT                                   28
```

( 2 ) INFORMATION FOR SEQ ID NO: 4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 4:

CTTCTAGCCT CCGCTAGTCA AAAATATT                                              28

( 2 ) INFORMATION FOR SEQ ID NO: 5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 5:

CTTCTAGCCT CCGCTAGTCA AAATT                                                 25

( 2 ) INFORMATION FOR SEQ ID NO: 6:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 6:

CTCCTTCTAG CCTCCGCTAG TCAAAAAT                                              28

( 2 ) INFORMATION FOR SEQ ID NO: 7:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 7:

CTCTCTCCTT CTAGCCTCCG CTAGTCAA                                              28

( 2 ) INFORMATION FOR SEQ ID NO: 8:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 8:

TTAATACTGA CGCTCTCGCA CCCATCT                                               27

( 2 ) INFORMATION FOR SEQ ID NO: 9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 9:

ACAACAGACG GGCACACACT AACT                                                  24

( 2 ) INFORMATION FOR SEQ ID NO: 10:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 10:

GAGAGAGCTC TGGTTTCCCT TT                                                       22

( 2 ) INFORMATION FOR SEQ ID NO: 11:

( i ) SEQUENCE CHARACTERISTICS:
      ( A ) LENGTH: 26 base pairs
      ( B ) TYPE: nucleic acid
      ( C ) STRANDEDNESS: single
      ( D ) TOPOLOGY: linear ( i i ) SEQUENCE DESCRIPTION: SEQ ID NO: 11:

TCGCCGCCCC TCGCCTCTTG CCGTGC                                                   26

( 2 ) INFORMATION FOR SEQ ID NO: 12:

( i ) SEQUENCE CHARACTERISTICS:
      ( A ) LENGTH: 26 base pairs
      ( B ) TYPE: nucleic acid
      ( C ) STRANDEDNESS: single
      ( D ) TOPOLOGY: linear ( i i ) SEQUENCE DESCRIPTION: SEQ ID NO: 12:

TCCTGCCATA GGAGATGCCT AAGGCC                                                   26

( 2 ) INFORMATION FOR SEQ ID NO: 13:

( i ) SEQUENCE CHARACTERISTICS:
      ( A ) LENGTH: 23 base pairs
      ( B ) TYPE: nucleic acid
      ( C ) STRANDEDNESS: single
      ( D ) TOPOLOGY: linear ( i i ) SEQUENCE DESCRIPTION: SEQ ID NO: 13:

TTGATGAGTC TGACTGTTCT GAT                                                      23

( 2 ) INFORMATION FOR SEQ ID NO: 14:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) SEQUENCE DESCRIPTION: SEQ ID NO: 14:

TTGGGAGGTG GGTTGCTTTG                                                          20

( 2 ) INFORMATION FOR SEQ ID NO: 15:

( i ) SEQUENCE CHARACTERISTICS:
      ( A ) LENGTH: 26 base pairs
      ( B ) TYPE: nucleic acid
      ( C ) STRANDEDNESS: single
      ( D ) TOPOLOGY: linear ( i i ) SEQUENCE DESCRIPTION: SEQ ID NO: 15:

TCTCTCTCTC CACCTTCTTC TTCTAT                                                   26

( 2 ) INFORMATION FOR SEQ ID NO: 16:

( i ) SEQUENCE CHARACTERISTICS:
      ( A ) LENGTH: 26 base pairs
      ( B ) TYPE: nucleic acid
      ( C ) STRANDEDNESS: single
      ( D ) TOPOLOGY: linear ( i i ) SEQUENCE DESCRIPTION: SEQ ID NO: 16:

TAATCGAATG GATCTGTCTC TGTCTC                                                   26

( 2 ) INFORMATION FOR SEQ ID NO: 17:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 17:

GAGCTCTTCG TCGCTGTCTC CGCTTCT     27

( 2 ) INFORMATION FOR SEQ ID NO: 18:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 18:

CTTCGGGCCT GTCGGGTCCC CTCGGG     26

( 2 ) INFORMATION FOR SEQ ID NO: 19:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 19:

GCCTGTCGGG TCC     13

( 2 ) INFORMATION FOR SEQ ID NO: 20:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 20:

GCCTGTCGGG TCCT     14

( 2 ) INFORMATION FOR SEQ ID NO: 21:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 21:

CGGGTCCCCT CGGG     14

( 2 ) INFORMATION FOR SEQ ID NO: 22:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 22:

GCCTGTCGGG TCCC     14

( 2 ) INFORMATION FOR SEQ ID NO: 23:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i i ) SEQUENCE DESCRIPTION: SEQ ID NO: 23:

CTTCGGGCCT GTCG                           14

( 2 ) INFORMATION FOR SEQ ID NO: 24:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) SEQUENCE DESCRIPTION: SEQ ID NO: 24:

CTTCGGGCCT GTCGGGTC                      18

( 2 ) INFORMATION FOR SEQ ID NO: 25:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) SEQUENCE DESCRIPTION: SEQ ID NO: 25:

GGGCCTGTCG GGTCCCCT                      18

( 2 ) INFORMATION FOR SEQ ID NO: 26:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) SEQUENCE DESCRIPTION: SEQ ID NO: 26:

CTGTCGGGTC CCCTCGGG                      18

( 2 ) INFORMATION FOR SEQ ID NO: 27:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) SEQUENCE DESCRIPTION: SEQ ID NO: 27:

TCGGGCCTGT CGGGTCCCCT CG                  22

( 2 ) INFORMATION FOR SEQ ID NO: 28:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) SEQUENCE DESCRIPTION: SEQ ID NO: 28:

CTTCGGGCCT GTCGGGTCCC CT                  22

( 2 ) INFORMATION FOR SEQ ID NO: 29:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) SEQUENCE DESCRIPTION: SEQ ID NO: 29:

GGGCCTGTCG GGTCCCCTCG GG    22

( 2 ) INFORMATION FOR SEQ ID NO: 30:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) SEQUENCE DESCRIPTION: SEQ ID NO: 30:

TAGGATCTAC TGGCTCCATT TC    22

( 2 ) INFORMATION FOR SEQ ID NO: 31:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) SEQUENCE DESCRIPTION: SEQ ID NO: 31:

ATTGGTACAA GCAGTTTTAG GCT    23

( 2 ) INFORMATION FOR SEQ ID NO: 32:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) SEQUENCE DESCRIPTION: SEQ ID NO: 32:

AGTGGTACAA GCAGTTTTAG GCT    23

( 2 ) INFORMATION FOR SEQ ID NO: 33:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) SEQUENCE DESCRIPTION: SEQ ID NO: 33:

GCTTCTTCCT GCCATAGGAG A    21

( 2 ) INFORMATION FOR SEQ ID NO: 34:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) SEQUENCE DESCRIPTION: SEQ ID NO: 34:

GACTGTTCTG ATGAGCTCTT CGTC    24

( 2 ) INFORMATION FOR SEQ ID NO: 35:

( i ) SEQUENCE CHARACTERISTICS:
    ( A ) LENGTH: 26 base pairs ( B ) TYPE: nucleic acid
        ( C ) STRANDEDNESS: single
        ( D ) TOPOLOGY: linear ( i i ) SEQUENCE DESCRIPTION: SEQ ID NO: 35:

GCCTATTCTG CTATGTCGAC ACCCAA                                                            2 6

( 2 ) INFORMATION FOR SEQ ID NO: 36:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 36:

CGGGCCTGTC GGGTCCCCTC GGGA                                                              2 4

( 2 ) INFORMATION FOR SEQ ID NO: 37:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 37:

CGGGCCTGTC GGGTCCCCTC GGGG                                                              2 4

( 2 ) INFORMATION FOR SEQ ID NO: 38:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 38:

TCTGCTATGT CGAC                                                                         1 4

( 2 ) INFORMATION FOR SEQ ID NO: 39:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 39:

ATGTCGACAC CCAA                                                                         1 4

( 2 ) INFORMATION FOR SEQ ID NO: 40:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 40:

GCCTATTCTG CTAT                                                                         1 4

( 2 ) INFORMATION FOR SEQ ID NO: 41:

( i ) SEQUENCE CHARACTERISTICS:
        ( A ) LENGTH: 18 base pairs
        ( B ) TYPE: nucleic acid
        ( C ) STRANDEDNESS: single ( D ) TOPOLOGY: linear ( i i ) SEQUENCE DESCRIPTION: SEQ ID NO: 41:

ATTCTGCTAT GTCGACAC                                                  18

( 2 ) INFORMATION FOR SEQ ID NO: 42:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 42:

TGCTATGTCG ACACCCAA                                                  18

( 2 ) INFORMATION FOR SEQ ID NO: 43:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 43:

GCCTATTCTG CTATGTCG                                                  18

( 2 ) INFORMATION FOR SEQ ID NO: 44:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 44:

GCCTATTCTG CTATGTCGAC AC                                             22

( 2 ) INFORMATION FOR SEQ ID NO: 45:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 45:

CTATTCTGCT ATGTCGACAC CC                                             22

( 2 ) INFORMATION FOR SEQ ID NO: 46:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 46:

ATTCTGCTAT GTCGACACCC AA                                             22

( 2 ) INFORMATION FOR SEQ ID NO: 47:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 47:

AGGCTTCATC ACGTGGACAT TGACG    25

( 2 ) INFORMATION FOR SEQ ID NO: 48:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 48:

CUUUCAGGUC CCUGUUCGGG CGCCACU    27

( 2 ) INFORMATION FOR SEQ ID NO: 49:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 49:

CUUUCAAGUC CCUGUUCGGG CGCCACU    27

( 2 ) INFORMATION FOR SEQ ID NO: 50:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 50:

CUUCUAGCCU CCGCUAGUCA AAAUUUUU    28

( 2 ) INFORMATION FOR SEQ ID NO: 51:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 51:

CUUCUAGCCU CCGCUAGUCA AAAAUAUU    28

( 2 ) INFORMATION FOR SEQ ID NO: 52:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 52:

CAUUUCCUAU CUUAGCGUUU CUUCCC    26

( 2 ) INFORMATION FOR SEQ ID NO: 53:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 53:

CUCCUUCUAG CCUCCGCUAG UCAAAAAU                28

( 2 ) INFORMATION FOR SEQ ID NO: 54:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 54:

CUCUCUCCUU CUAGCCUCCG CUAGUCAA                28

( 2 ) INFORMATION FOR SEQ ID NO: 55:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 55:

UUAAUACUGA CGCUCUCGCA CCCAUCU                 27

( 2 ) INFORMATION FOR SEQ ID NO: 56:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 56:

ACAACAGACG GGCACACACU AACU                    24

( 2 ) INFORMATION FOR SEQ ID NO: 57:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 57:

GAGAGAGCUC UGGUUUCCCU UU                      22

( 2 ) INFORMATION FOR SEQ ID NO: 58:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 58:

GUCAGUGAUA GUCCAAGUUG GC                      22

( 2 ) INFORMATION FOR SEQ ID NO: 59:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 59:

UCCUGCCAUA GGAGAUGCCU AAGGCC                  26

( 2 ) INFORMATION FOR SEQ ID NO: 60:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) SEQUENCE DESCRIPTION: SEQ ID NO: 60:

UUGAUGAGUC UGACUGUUCU GAU      23

( 2 ) INFORMATION FOR SEQ ID NO: 61:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) SEQUENCE DESCRIPTION: SEQ ID NO: 61:

UUGGGAGGUG GGUUGCUUUG      20

( 2 ) INFORMATION FOR SEQ ID NO: 62:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) SEQUENCE DESCRIPTION: SEQ ID NO: 62:

UCUCUCUCUC CACCUUCUUC UUCUAU      26

( 2 ) INFORMATION FOR SEQ ID NO: 63:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) SEQUENCE DESCRIPTION: SEQ ID NO: 63:

UAAUCGAAUG GAUCUGUCUC UGUCUC      26

( 2 ) INFORMATION FOR SEQ ID NO: 64:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) SEQUENCE DESCRIPTION: SEQ ID NO: 64:

GAGCUCUUCG UCGCUGUCUC CGCUUCU      27

( 2 ) INFORMATION FOR SEQ ID NO: 65:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) SEQUENCE DESCRIPTION: SEQ ID NO: 65:

CUUCGGGCCU GUCGGUCCC CUCGGG      26

( 2 ) INFORMATION FOR SEQ ID NO: 66:

( i ) SEQUENCE CHARACTERISTICS:
  ( A ) LENGTH: 13 base pairs
  ( B ) TYPE: nucleic acid
  ( C ) STRANDEDNESS: single
  ( D ) TOPOLOGY: linear ( i i ) SEQUENCE DESCRIPTION: SEQ ID NO: 66:

GCCUGUCGGG UCC 13

( 2 ) INFORMATION FOR SEQ ID NO: 67:

( i ) SEQUENCE CHARACTERISTICS:
  ( A ) LENGTH: 14 base pairs
  ( B ) TYPE: nucleic acid
  ( C ) STRANDEDNESS: single
  ( D ) TOPOLOGY: linear ( i i ) SEQUENCE DESCRIPTION: SEQ ID NO: 67:

GCCUGUCGGG UCCU 14

( 2 ) INFORMATION FOR SEQ ID NO: 68:

( i ) SEQUENCE CHARACTERISTICS:
  ( A ) LENGTH: 14 base pairs
  ( B ) TYPE: nucleic acid
  ( C ) STRANDEDNESS: single
  ( D ) TOPOLOGY: linear ( i i ) SEQUENCE DESCRIPTION: SEQ ID NO: 68:

CGGGUCCCCU CGGG 14

( 2 ) INFORMATION FOR SEQ ID NO: 69:

( i ) SEQUENCE CHARACTERISTICS:
  ( A ) LENGTH: 14 base pairs
  ( B ) TYPE: nucleic acid
  ( C ) STRANDEDNESS: single
  ( D ) TOPOLOGY: linear ( i i ) SEQUENCE DESCRIPTION: SEQ ID NO: 69:

GCCUGUCGGG UCCC 14

( 2 ) INFORMATION FOR SEQ ID NO: 70:

( i ) SEQUENCE CHARACTERISTICS:
  ( A ) LENGTH: 14 base pairs
  ( B ) TYPE: nucleic acid
  ( C ) STRANDEDNESS: single
  ( D ) TOPOLOGY: linear ( i i ) SEQUENCE DESCRIPTION: SEQ ID NO: 70:

CUUCGGGCCU GUCG 14

( 2 ) INFORMATION FOR SEQ ID NO: 71:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( i i ) SEQUENCE DESCRIPTION: SEQ ID NO: 71:

CUUCGGGCCU GUCGGGUC 18

( 2 ) INFORMATION FOR SEQ ID NO: 72:

( i ) SEQUENCE CHARACTERISTICS:

( A ) LENGTH: 18 base pairs
( B ) TYPE: nucleic acid
( C ) STRANDEDNESS: single
( D ) TOPOLOGY: linear ( i i ) SEQUENCE DESCRIPTION: SEQ ID NO: 72:

GGGCCUGUCG GGUCCCCU                                             18

( 2 ) INFORMATION FOR SEQ ID NO: 73:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) SEQUENCE DESCRIPTION: SEQ ID NO: 73:

CUGUCGGGUC CCCUCGGG                                             18

( 2 ) INFORMATION FOR SEQ ID NO: 74:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) SEQUENCE DESCRIPTION: SEQ ID NO: 74:

UCGGGCCUGU CGGGUCCCCU CG                                        22

( 2 ) INFORMATION FOR SEQ ID NO: 75:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) SEQUENCE DESCRIPTION: SEQ ID NO: 75:

CUUCGGGCCU GUCGGGUCCC CU                                        22

( 2 ) INFORMATION FOR SEQ ID NO: 76:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) SEQUENCE DESCRIPTION: SEQ ID NO: 76:

GGGCCUGUCG GGUCCCCUCG GG                                        22

( 2 ) INFORMATION FOR SEQ ID NO: 77:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) SEQUENCE DESCRIPTION: SEQ ID NO: 77:

UAGGAUCUAC UGGCUCCAUU UC                                        22

( 2 ) INFORMATION FOR SEQ ID NO: 78:

( i ) SEQUENCE CHARACTERISTICS:
( A ) LENGTH: 23 base pairs
( B ) TYPE: nucleic acid 5,629,413

47                                                                48

-continued ( C ) STRANDEDNESS: single
            ( D ) TOPOLOGY: linear ( i i ) SEQUENCE DESCRIPTION: SEQ ID NO: 78:

AUUGGUACAA GCAGUUUUAG GCU                                             23

( 2 ) INFORMATION FOR SEQ ID NO: 79:

( i ) SEQUENCE CHARACTERISTICS:
            ( A ) LENGTH: 23 base pairs
            ( B ) TYPE: nucleic acid
            ( C ) STRANDEDNESS: single
            ( D ) TOPOLOGY: linear ( i i ) SEQUENCE DESCRIPTION: SEQ ID NO: 79:

AGUGGUACAA GCAGUUUUAG GCU                                             23

( 2 ) INFORMATION FOR SEQ ID NO: 80:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) SEQUENCE DESCRIPTION: SEQ ID NO: 80:

GCUUCUUCCU GCCAUAGGAG A                                               21

( 2 ) INFORMATION FOR SEQ ID NO: 81:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) SEQUENCE DESCRIPTION: SEQ ID NO: 81:

GACUGUUCUG AUGAGCUCUU CGUC                                            24

( 2 ) INFORMATION FOR SEQ ID NO: 82:

( i ) SEQUENCE CHARACTERISTICS:
            ( A ) LENGTH: 26 base pairs
            ( B ) TYPE: nucleic acid
            ( C ) STRANDEDNESS: single
            ( D ) TOPOLOGY: linear ( i i ) SEQUENCE DESCRIPTION: SEQ ID NO: 82:

GCCUAUUCUG CUAUGUCGAC ACCCAA                                          26

( 2 ) INFORMATION FOR SEQ ID NO: 83:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) SEQUENCE DESCRIPTION: SEQ ID NO: 83:

CGGGCCUGUC GGGUCCCCUC GGGA                                            24

( 2 ) INFORMATION FOR SEQ ID NO: 84:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) SEQUENCE DESCRIPTION: SEQ ID NO: 84:

CGGGCCUGUC GGGUCCCCUC GGGG                                    24

( 2 ) INFORMATION FOR SEQ ID NO: 85:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 85:

UCUGCUAUGU CGAC                                               14

( 2 ) INFORMATION FOR SEQ ID NO: 86:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 86:

AUGUCGACAC CCAA                                               14

( 2 ) INFORMATION FOR SEQ ID NO: 87:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 87:

GCCUAUUCUG CUAU                                               14

( 2 ) INFORMATION FOR SEQ ID NO: 88:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 88:

AUUCUGCUAU GUCGACAC                                           18

( 2 ) INFORMATION FOR SEQ ID NO: 89:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 89:

UGCUAUGUCG ACACCCAA                                           18

( 2 ) INFORMATION FOR SEQ ID NO: 90:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 90:

```
GCCUAUUCUG CUAUGUCG                                                  18
```

( 2 ) INFORMATION FOR SEQ ID NO: 91:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 91:

```
GCCUAUUCUG CUAUGUCGAC AC                                             22
```

( 2 ) INFORMATION FOR SEQ ID NO: 92:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 92:

```
CUAUUCUGCU AUGUCGACAC CC                                             22
```

( 2 ) INFORMATION FOR SEQ ID NO: 93:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 93:

```
AUUCUGCUAU GUCGACACCC AA                                             22
```

( 2 ) INFORMATION FOR SEQ ID NO: 94:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 94:

```
UUGGGUGUCG ACAUAGCAGA AUAGGC                                         26
```

( 2 ) INFORMATION FOR SEQ ID NO: 95:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 95:

```
CCCGAGGGGA CCCGACAGGC CCGAAG                                         26
```

1. An oligonucleotide which inhibits HIV replication consisting of the sequence

SEQ ID NO: 18: CTTCGGGCCT GTCGGGTCCC CTCGGG.

2. The oligonucleotide of claim 1, wherein said oligonucleotide comprises one or more modified internucleoside linkages which are phosphorothioate linkages.

3. The oligonucleotide of claim 2, wherein said oligonucleotide is predominantly comprised of said one or more modified internucleoside linkages which are phosphorothioate linkages.

4. The oligonucleotide of claim 3, wherein said oligonucleotide is wholly comprised of said modified internucleoside linkages which are phosphorothioate linkages.

* * * * *

UNITED STATES PATENT AND TRADEMARK OFFICE
CERTIFICATE OF CORRECTION

PATENT NO. : 5,629,413
DATED : May 13, 1997
INVENTOR(S) : Todd C. Peterson, et. al.

It is certified that error appears in the above-identified patent and that said Letters Patent is hereby corrected as shown below:

Column 1, Line 33: Delete "vital" and insert --viral--

Column 8, Line 1: Delete "internucleotide" and insert --internucleoside--

Column 14, Line 44: Delete "containing" and insert --contain--

Signed and Sealed this

Thirtieth Day of June, 1998

Attest:

BRUCE LEHMAN

Attesting Officer

Commissioner of Patents and Trademarks